United States Patent
Kuo et al.

(10) Patent No.: US 9,714,887 B2
(45) Date of Patent: Jul. 25, 2017

(54) DETECTION METHOD FOR SUBSTANCE AND SYSTEM THEREOF

(75) Inventors: Chi-Wen Kuo, Taipei (TW); Yu-Kun Hung, Hsinchu (TW); Tzu-Sou Chuang, Hsinchu (TW)

(73) Assignee: Taiwan Semiconductor Manufacturing Company, Ltd., Hsinchu (TW)

(*) Notice: Subject to any disclaimer, the term of this patent is extended or adjusted under 35 U.S.C. 154(b) by 674 days.

(21) Appl. No.: 13/602,528

(22) Filed: Sep. 4, 2012

(65) Prior Publication Data
US 2014/0065719 A1  Mar. 6, 2014

(51) Int. Cl.
G01N 31/22 (2006.01)
G01N 1/22 (2006.01)
G01N 21/82 (2006.01)

(52) U.S. Cl.
CPC ............ G01N 1/2202 (2013.01); G01N 21/82 (2013.01); G01N 31/22 (2013.01)

(58) Field of Classification Search
CPC ....... G01N 1/2202; G01N 21/82; G01N 31/22
USPC ............................ 436/149, 163, 164; 422/83
See application file for complete search history.

(56) References Cited

U.S. PATENT DOCUMENTS

| | | | | |
|---|---|---|---|---|
| 4,466,942 A * | 8/1984 | Rogers | ................... | G01N 30/00 422/430 |
| 6,787,366 B1 * | 9/2004 | Novak | ........................ | 436/162 |
| 2003/0235926 A1 * | 12/2003 | Knollenberg | ........ | G01N 29/222 436/181 |
| 2004/0035183 A1 * | 2/2004 | O'Brien et al. | ............. | 73/23.36 |
| 2005/0183490 A1 * | 8/2005 | Grayfer | ................. | B01D 53/22 73/23.2 |

FOREIGN PATENT DOCUMENTS

| | | |
|---|---|---|
| CN | 101718706 B | 4/2012 |
| TW | 200301353 | 11/2002 |

OTHER PUBLICATIONS

Determination of boron with chromotropic acid by first-derivative synchronous spectrofluorimetry Fermin Capitan, Alberto Navalon, Eloisa Manzano, Luis F. Capitan, and Jose L. Vilchez Fresenius J Anal Chem (1991) 340: 6-10.*

Pressure-assisted chelation extraction of lead from contaminated soil P.K. Andy Hong, Xiaoxiao Cai, and Zhixiong Cha Environmental Pollution 153 (2008) 14-21.*

Hong et al. "Pressure-assisted chelation extraction of lead from contaminated soil" Environmental Pollution vol. 153, Issue 1, pp. 14-21 (May 2008).

* cited by examiner

Primary Examiner — Krishnan S Menon
Assistant Examiner — Dwan A Gerido
(74) Attorney, Agent, or Firm — WPAT, P.C., Intellectual Property Attorneys; Anthony King

(57) ABSTRACT

A detection method for a substance and a system thereof are provided. The detection method for a substance contained in a sample includes providing a reagent in reaction with the substance to form a chelate; and pressurizing the substance to accumulate the chelate.

16 Claims, 4 Drawing Sheets

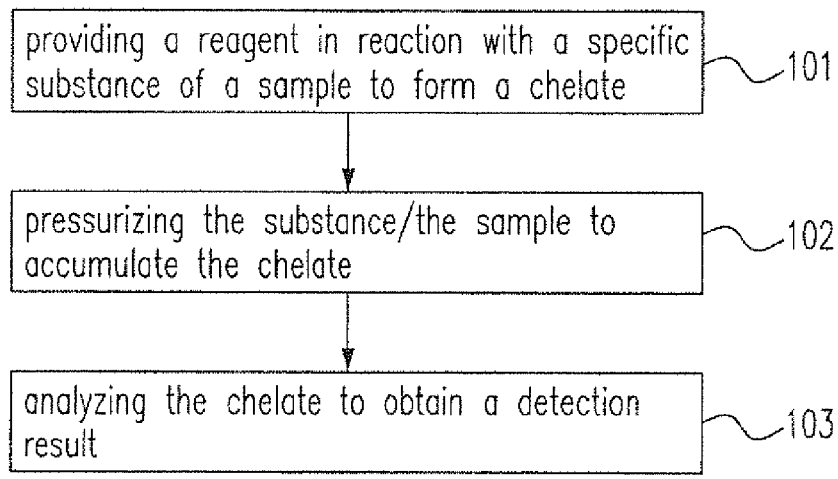
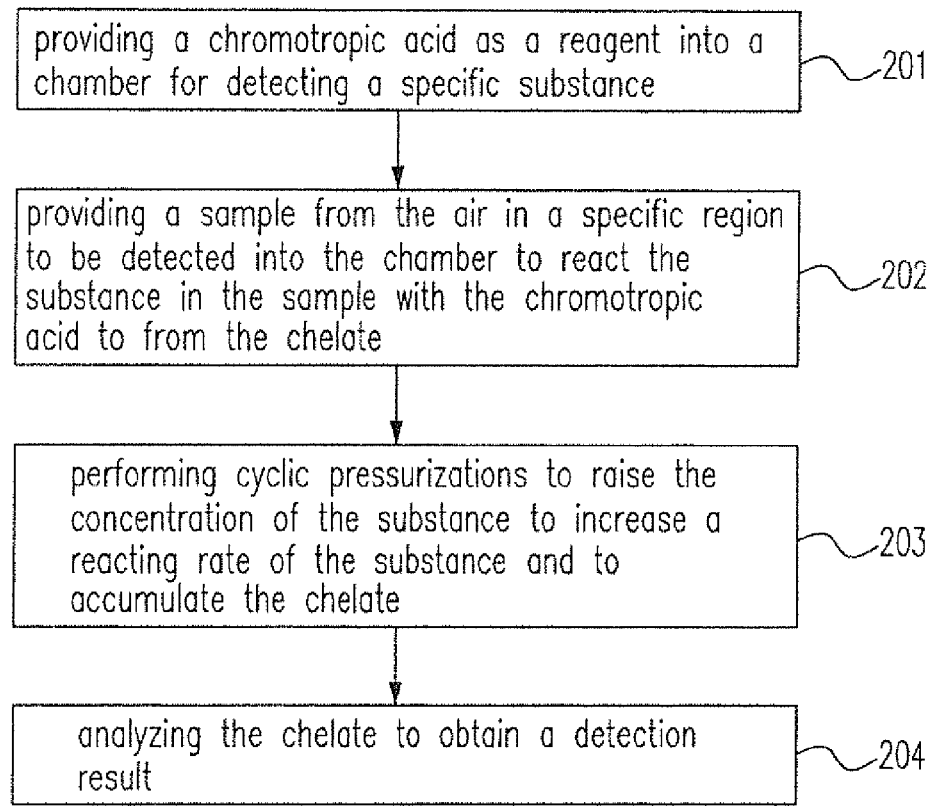

DETECTION METHOD FOR SUBSTANCE AND SYSTEM THEREOF

FIELD

The present disclosure relates to an air detection method and a system thereof. More particularly, it relates to an airborne molecular contamination (AMC) detection method and an AMC detection system.

BACKGROUND

It is known that air contaminants are harmful to the health, especially to children or pregnant women. In addition, the air contaminants also damage electronic products. Taking the airborne molecular contamination (AMC) for example, the AMC includes four types in relation to the main chemical natures thereof as follows: (1) Molecular Acids (MA) include a fluoride, a chloride, a bromide, a sulfate, a phosphate, a nitrogen oxide and so on; (2) Molecular Bases (MB) include ammonia, an amine, an amide, a urea and so on; (3) Molecular Condensables (MC) include a plasticizer, an antioxidant, a phosphate, a siloxane and so on; and (4) Molecular Dopants (MD) include a boron, a phosphorous, an arsenic, an antimony and so on. These contaminants are harmful to not only the manufactures and/or the experiments but also to the operators and/or the researchers in the cleanroom or the laboratory, so that an air detection method is essential to know whether the air in a specific space is polluted or not.

An existing method for detecting a boron or phosphorous contaminant is to put a testing wafer in the cleanroom for twenty four hours to collect the contaminant, and at the mean time, the contaminant reacts with the silicon on the wafer. Then, the testing wafer is taken to the laboratory for the analysis to find a detection result. It can be seen that this method cost much time to get the detection result.

Another existing method is to apply an impinger to get an AMC sample in the cleanroom, but it suffers from a low concentration and low adsorption issue. In the low concentration situation, it usually takes twenty four hours to get the sample in the cleanroom for the analysis. Therefore, this method is also time-consuming and has a poor precision.

There are still many other existing detection methods, such as Fourier Transform infrared spectroscopy (FTIR) sampling, for detecting air pollution. However, many existing detection methods spend much time to get a detection result, and some other existing detection methods cost a lot to get a detection result and are subject to the concentration limit.

There is a need to solve the above-mentioned deficiencies/issues.

SUMMARY

In accordance with one aspect of the present disclosure, a detection method for a substance contained in a sample under detection comprises steps of providing a reagent in reaction with the substance to form a chelate; and pressurizing the substance to accumulate the chelate.

In accordance with another aspect of the present disclosure, a detection method for a sample with a substance under detection comprises steps of: providing a reagent in reaction with the sample; fastening a reaction of the sample and the reagent; and analyzing the reagent to determine whether the sample contains the substance.

In accordance with yet another aspect of the present disclosure, a detection system for a substance, comprises: a chamber containing a reagent in reaction with the substance to form a chelate; and a pumping device coupled to and performing cyclic pressurizations for the chamber to accumulate the chelate.

The present disclosure may best be understood through the following descriptions with reference to the accompanying drawings, in which:

DESCRIPTION OF THE DRAWINGS

FIG. 1 is a flow chart illustrating an embodiment in accordance with the present disclosure.

FIG. 2 is a flow chart illustrating another embodiment in accordance with the present disclosure.

DETAILED DESCRIPTION

Figure 3:
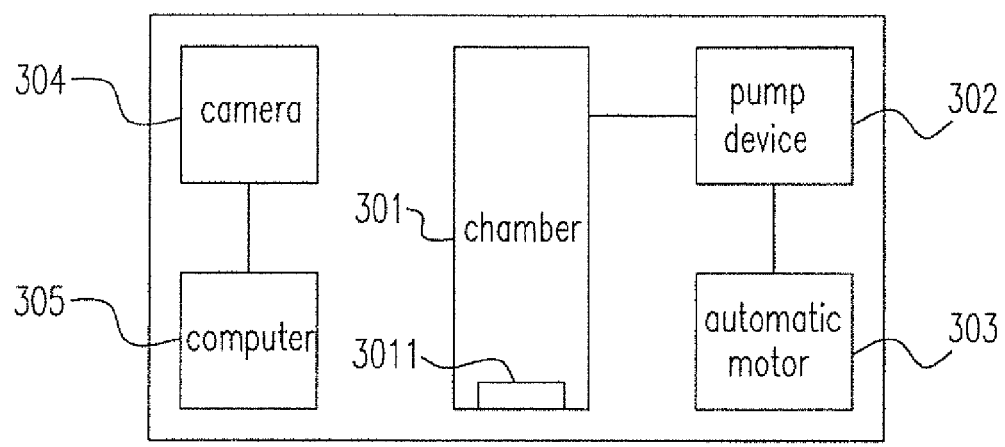
FIG. 3 is a schematic diagram illustrating a system embodiment in accordance with the present disclosure.

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments described herein are capable of operation in other orientations than described or illustrated herein.

It is to be noticed that the term "including", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device including means A and B" should not be limited to devices consisting only of components A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments may be practiced without these specific details. In other instances, well-known methods, structures and techniques have not been shown in detail in order not to obscure an understanding of this description.

The disclosure will now be described by a detailed description of several embodiments. It is clear that other embodiments can be configured according to the knowledge of persons skilled in the art without departing from the true technical teaching of the present disclosure, the claimed disclosure being limited only by the terms of the appended claims.

Please refer to FIG. 1, which is a flow chart illustrating an embodiment in accordance with the present disclosure. The embodiment is a detection method 100. The detection method 100 is used to detect a specific substance in the air in a specific region, such as a cleanroom, a laboratory or a workroom. The detection method 100 includes the following steps 101~103. The step 101 is to provide a reagent in reaction with a specific substance of a sample to form a chelate; the step 102 is to pressurize the substance/the sample to accumulate the chelate; and the step 103 is to analyze the chelate to obtain a detection result.

In step 101, the reagent can be a solution or a testing piece to react with the specific substance to form the chelate. It is known that the contaminants of the AMC usually have the corresponding chelating agent (in a solid or liquid state) to form a chelate. For example, in order to detect a sulfate belonging to MA, the reagent can include a barium perchlorate and a Thorin indicator to form a chelate. In order to detect an amide belonging to MB, the reagent includes a Phenolsodiumnitroprusside and a sodium hypochlorite to form an indophenol blue.

In step 102, the concentration is raised on site by pressurizing the substance/the sample (Dalton law of additive pressure) via a hand pump or any device having the function of pressurizing, since the process of pressurizing is fast. If the performing pressurization cycles are applied to the detection method, it can raise the concentration to more than 240 times in each pressurization cycle. When the concentration increases, the reacting rate of the substance to be detected and the reagent also increases, so that the formed chelate will accumulate rapidly. Furthermore, due to the property of the chelate, the chelate will not reverse when the additive pressure is released or when the next pressurization cycle is performed. In other words, the accumulated chelate will not decrease when the environment changes, so that the following analysis would be easier and more precise.

In step 103, the formed chelate can be analyzed by many analysis methods, such as a titrimetric analysis, a pH value analysis, a conductivity analysis, a spectrum analysis and so on. Therefore, the concentration of the specific substance in the detected air could be known by these methods.

Accordingly, the whole detection procedure from sampling to analysis could be taken on site. Namely, the present detection method is an instant (less than 10 minutes) and precise detection method to respond the contamination, especially for AMC in the cleanroom. Furthermore, the detection method is also applicable to the scrubber efficiency measurement, such that the scrubber efficiency can be obtained on site.

Please refer to FIG. 2, which is a flow chart illustrating another embodiment in accordance with the present disclosure. The embodiment is a detection method 200. The detection method 200 includes the following steps 201~204. The step 201 is to provide a chromotropic acid as a reagent into a chamber for detecting a specific substance; the step 202 is to provide a sample from the air in a specific region to be detected into the chamber to react the substance in the sample with the chromotropic acid to form the chelate; the step 203 is to perform cyclic pressurizations to raise the concentration of the substance to increase a reacting rate of the substance and to accumulate the chelate; and the step 204 is to analyze the chelate to obtain a detection result.

In the steps 201 and 202, for example, the reagent is a solution containing the chromotropic acid or a testing piece coated with the chromotropic acid, and the chromotropic acid is chosen to detect the specific substances (every substance usually has its own chromotropic acid for detection). Furthermore, the chamber is used to isolate the sample of the air to be detected from the external environment so as to keep the sample away from being affected by the air of the external environment.

In the step 203, the cyclic pressurizations can be performed by a pump to input a known gas or air, such as pure air or the above-mentioned air to be detected, into the chamber to raise the concentration of the sample/the substance or to increase the pressure of the chamber. For example, each cycle raises the pressure to 1469 psi, about 100 atm, by a hand pump, or to at least 3600 psi via a pump driven by an automatic motor. By performing one pressurization or the cyclic pressurizations, the environment of the chamber would be changed to a desired condition, and the reacting rate and the amount of the formed chelate can be controlled accordingly. Namely, the maximum amount of the formed chelate in the initial condition, i.e. the condition before the pressurization, would increase after the pressurization. Since the process of forming the chelate is an irreversible reaction, the formed chelate will not react to form the specific substance and the chromotropic acid when the condition of the chamber changes, such as releasing the pressure of the chamber. Therefore, it is beneficial to the following analysis because the accumulated chelate makes the analysis easier and more precise.

In the step 204, the formed chelate in the step 203 is used to be analyzed to obtain the information of the detected air by any analysis method, such as the above-mentioned methods. Moreover, the changed conditions of the chamber in the step 203 can be controlled and are known, so that the concentration of the specific substance in the detected air can be derived from the detection results of the step 204. In addition, a camera is used to take the pictures of the formed chelate to generate an image data for an analysis. For example, a testing piece with the chromotropic acid is taken a photograph by the camera before putted into the chamber to generate a reference image data, and then after the testing piece is putted into the chamber and reacts with the sample, the testing piece is shot by the camera to generate a detection image data, which can be compared with the reference image data to obtain the detection results.

Please refer to FIG. 3, which is a schematic diagram illustrating a system embodiment in accordance with the present disclosure. The system embodiment is a detection system 300 for detecting a substance, and it is also used in the cleanroom for AMC detection. The detection system 300 includes a chamber 301 with a reagent 3011, a pump device 302, an automatic motor 303, a camera 304 and a computer 305.

The chamber 301 is configured to contain a sample from an air to be detected and the reagent 3011 reacting with a specific substance, the pump device 302 is coupled to the chamber 301 to raise the pressure of the chamber 301, the automatic motor 303 is coupled to the pump device 302 to drive the pump device 302, the camera 304 is configured to take the picture of the reagent to generate an image data, and the computer 305 is configured to receive the image data from the camera 304 for analysis. It is noted that the pump device 302 can be configured to input either a known gas or the air to be detected into the chamber 301 to increase the pressure of the chamber.

Figure 4:
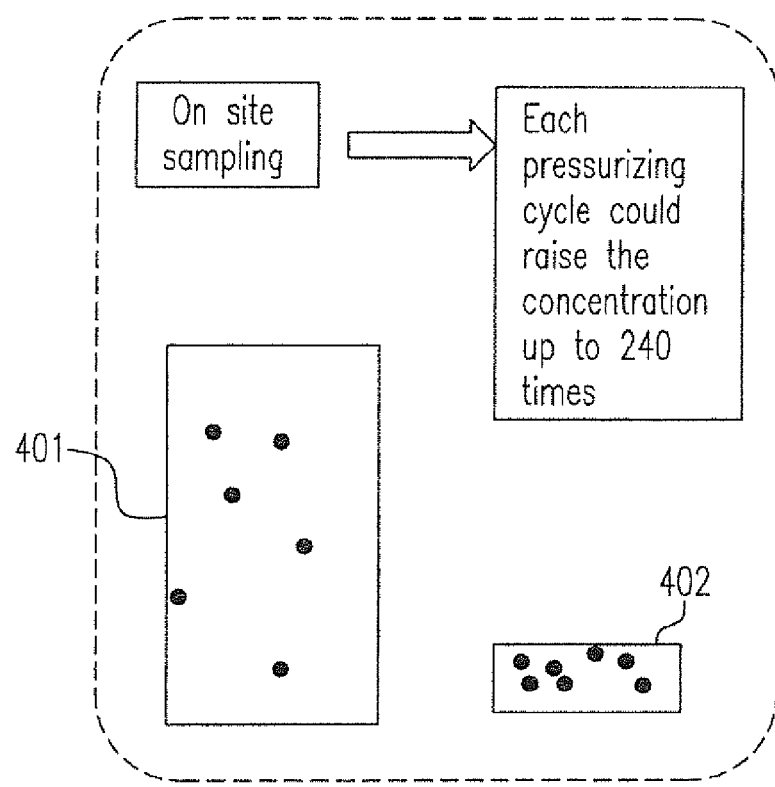
FIG. 4 is a schematic diagram illustrating the pressurizing process in accordance with the system embodiment.

Taking the detection of boron belonging to MD for example, the boron reacts with the chromotropic acid to form a stable chelate. The chamber 301 is, for example, a stainless high pressure chamber for setting therein a boron reagent and a sample from the air of a specific region to be detected, and the reagent 3011 is a solution containing the chromotropic acid or a plate with the chromotropic acid. The pump device 302 is either a high pressure air pump or a hand pump to raise the additive pressure of the boron in the chamber 301 for each pressurization cycle. Please refer to FIG. 4, which is a schematic diagram illustrating the pressurizing process in accordance with the system embodiment. The initial concentration 401 represents the concentration of the sample from the detected air in the chamber 301 before a cyclic pressurization is performed, where the dot represents the boron. The concentration 402 after using the pump device 302 to perform the pressurizing cycle raises up to 240 times. In other words, it means that the pump device 302 fastens the reacting rate of the boron and the chromotropic acid either in the solution or on the plate, so that the chelate is obtained quickly and on site. It is noted that when performing the repeated decompressions and pressurizations, the chelate formed by the boron and the chromotropic acid will not generate boron back into the gas phase during the decompressions since the reaction of forming the chelate is an irreversible reaction. The camera 304 is for example, a charge-coupled device (CCD) utilized to take the digital image pixels of either the plate or the solution having the chromotropic acid and the formed chelate. The computer 305 is used to amplify the digital image pixel data for analyzing the data to compute the initial concentration of the boron in the sample, so that the concentration of the boron in the detected air is obtained as well. In addition, the computer 305 is also used to calibrate the detection results.

Figure 5:
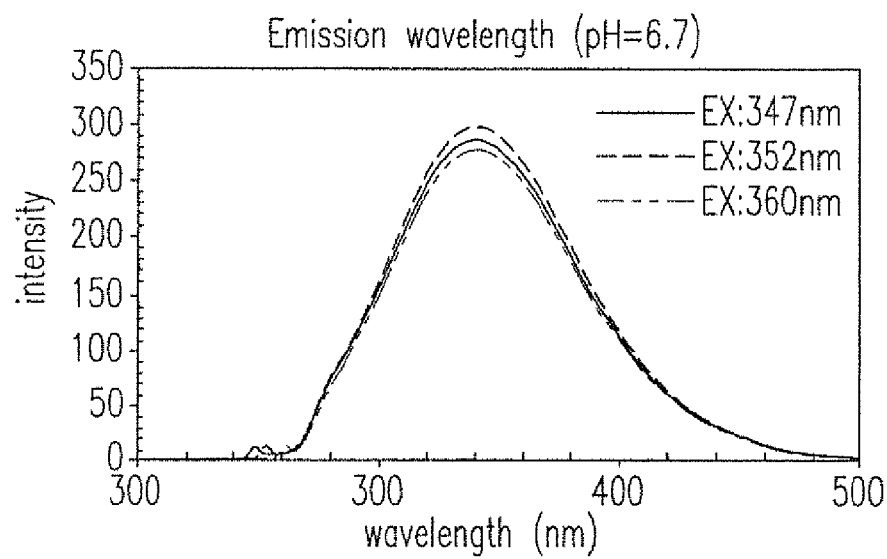
FIG. 5 is the intensity-wavelength curve chart before the chromotropic acid reacts with the boron.
Figure 6:
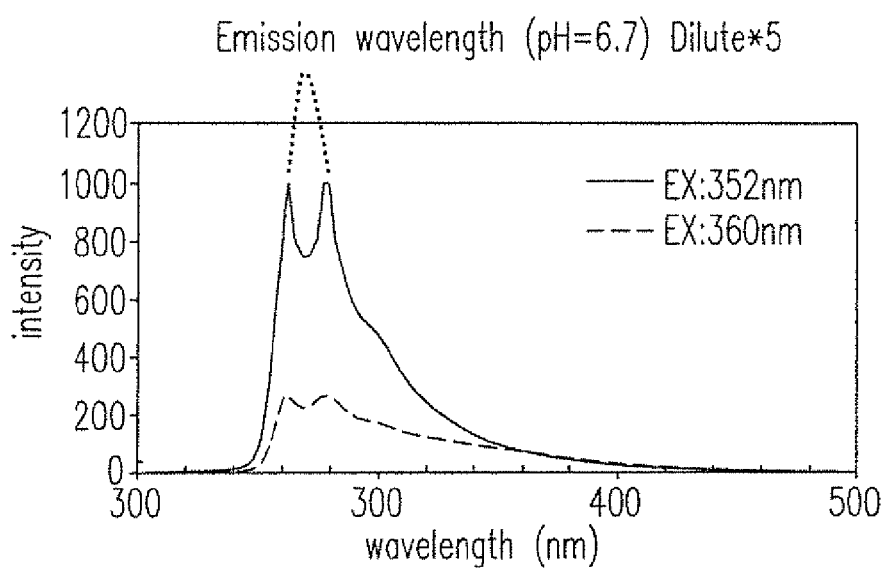
FIG. 6 is the intensity-wavelength curve chart after the chromotropic acid reacts with the boron.

There is still another analysis method. Take the optical analysis method as an example. Please refer to FIG. 5, which illustrates the intensity-wavelength curve chart before the chromotropic acid reacts with the boron. The pH value of the solution containing the chromotropic acid is adjusted to 6.7 by adding a buffer solution thereinto. FIG. 5 shows the spectrum from 300 nm to 600 nm of the emission of the chromotropic acid with the pH value of 6.7 excited by the three lights respectively having the wavelengths 347 nm, 352 nm and 360 nm. It is observed that the emission from the chromotropic acid excited by the light with the wavelength 352 nm has the strongest intensity, and the peak is at 440 nm, so that the light with the 352 nm wavelength is a better choice for analysis. Please refer to FIG. 6, which illustrates the intensity-wavelength curve chart after the chromotropic acid reacts with the boron. The solution containing the chromotropic acid is diluted by 5 times. FIG. 6 shows the spectrum of the emission of the chromotropic acid, after reacting with the boron, excited by the two lights respectively having the wavelengths 352 nm and 360 nm. The dotted line in the curve chart 600 shows the emission of the chromotropic acid, before reacting with the boron, excited by the light having the wavelength 352 nm, so that the concentration of the boron can be obtained by comparing the dotted line and the solid line.

Figure 7:
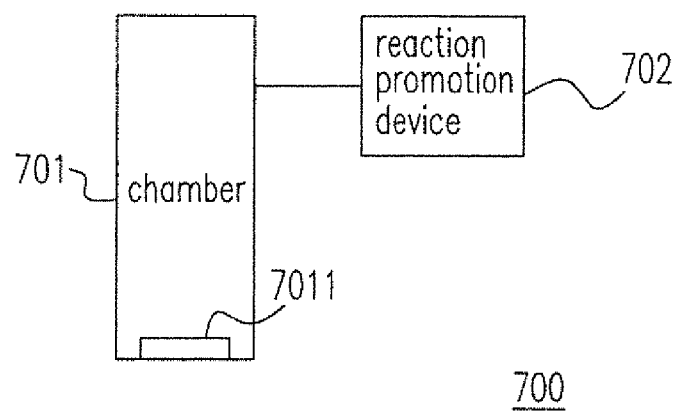
FIG. 7 is a schematic diagram illustrating another system embodiment in accordance with the present disclosure.

Please refer to FIG. 7, which is a schematic diagram illustrating another system embodiment in accordance with the present disclosure. The system embodiment is a detection system 700 for detecting a specific substance. The detection system 700 includes a chamber 701 with a reagent 7011, and a reaction promotion device 702 coupled to the chamber 701. The chamber 701 is configured to contain an air sample to be detected, and the reagent 7011 is used to check whether the air sample contains the specific substance. The reaction promotion device 702 is configured to fasten the reaction of the sample and the reagent 7011, so that a compound formed by the sample and the reagent for analysis is obtained more quickly. Furthermore, the reaction promotion device 702 is e.g. a concentration promotion device, a pumping device or any other device having the function of increasing the reaction rate.

There are further embodiments provided as follows.

Embodiment 1: a detection method for a substance contained in a sample under detection includes steps of: providing a reagent in reaction with the substance to form a chelate; and pressurizing the substance to accumulate the chelate.

Embodiment 2: the detection method according to the above-mentioned embodiment further includes a step of analyzing the chelate, wherein the reagent is one of a solution and a testing piece and the pressurizing step is performed by a pump.

Embodiment 3: the detection method according to one of the above-mentioned embodiments, wherein the testing piece is a solid chelating agent.

Embodiment 4: the detection method according to any one of the above-mentioned embodiments, wherein the providing step further includes steps of: providing a chromotropic acid as the reagent into a chamber; and providing the sample containing the substance having a concentration into the chamber to react the substance with the chromotropic acid to form the chelate, and the pressurizing step further includes a step of: performing cyclic pressurizations to raise the concentration of the substance to increase a reacting rate of the substance and accumulate the chelate.

Embodiment 5: the detection method according any one of the above-mentioned embodiments, wherein the acid providing step further includes a step of providing a solution having the chromotropic acid in the chamber.

Embodiment 6: the detection method according to any one of the above-mentioned embodiments, wherein the acid providing step further includes a step of adding a buffer solution into the solution.

Embodiment 7: the detection method according to any one of the above-mentioned embodiments, wherein the acid providing step further includes a step of providing a testing piece with the chromotropic acid in the chamber.

Embodiment 8: the detection method according to any one of the above-mentioned embodiments further includes a step of performing a decompression for the chamber, wherein the chelate is free from a reverse reaction after the decompression.

Embodiment 9: the detection method according to any one of the above-mentioned embodiments further includes a step of analyzing the chelate, wherein the analyzing step is performed by an analyzing method being one selected from a group consisting of a titrimetric analysis, a pH value analysis, a conductivity analysis, a spectrum analysis and a combination thereof.

Embodiment 10: the detection method according to any one of the above-mentioned embodiments further includes steps of taking image pixels of the chromotropic acid and the chelate to generate a pixel data and analyzing the pixel data.

Embodiment 11: the detection method according to any one of the above-mentioned embodiments further includes a step of analyzing the formed chelate to determine the original concentration of the substance in the sample.

Embodiment 12: the detection method according to any one of the above-mentioned embodiments, wherein the substance is an airborne molecular contaminant (AMC).

Embodiment 13: the detection method according to any one of the above-mentioned embodiments is applied to a scrubber efficiency measurement.

Embodiment 14: a detection method for a sample with a substance under detection includes steps of: providing a reagent in reaction with the sample; fastening a reaction of the sample and the reagent; and analyzing the reagent to determine whether the sample contains the substance.

Embodiment 15: the detection method according to the above-mentioned embodiment, wherein the fastening step is performed by a pressurization.

Embodiment 16: a detection system for a substance includes: a chamber containing a reagent in reaction with the substance to form a chelate; and a pumping device coupled to and performing cyclic pressurizations for the chamber to accumulate the chelate.

Embodiment 17: the detection system according to the above-mentioned embodiment further includes an automatic motor to drive the pumping device.

Embodiment 18: the detection system according to one of the above-mentioned embodiments further includes a computer to analyze the chelate.

Embodiment 19: the detection system according to any one of the above-mentioned embodiments further includes a camera to take image pixels for the reagent and the chelate to generate a pixel data.

Embodiment 20: the detection method according to any one of the above-mentioned embodiments, wherein the reagent further comprises a chromotropic acid.

While the disclosure has been described in terms of what are presently considered to be the most practical and preferred embodiments, it is to be understood that the disclosure need not be limited to the disclosed embodiment. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present disclosure which is defined by the appended claims.

What is claimed is:

1. A detection method for airborne molecular substance contained in a sample under a clean room setting, comprising steps of:
   providing a chromotropic acid in reaction with the airborne molecular substance from the clean room to form a chelate in a chamber;
   raising a concentration of the airborne molecular substance to increase a reacting rate of the airborne molecular substance and the chromotropic acid and accumulate the chelate through performing cyclic pressurization by a pump, the cyclic pressurization raising a pressure of the chamber to at least 3600 psi per cycle; and
   determining the concentration of airborne molecular substance by taking image pixels of the chromotropic acid and the chelate to generate a pixel data and analyzing the pixel data,
   wherein the airborne molecular substance comprises molecular acids, molecular bases, molecular condensables, or molecular dopants in the clean room,
   wherein the raising the concentration of the airborne molecular substance by raising a pressure of the chamber to at least 3600 psi per cycle renders obtaining a detection result from providing the chromotropic acid in reaction with the airborne molecular substance to analyzing the pixel data in less than 10 minutes.

2. The detection method as claimed in claim 1, wherein the providing the chromotropic acid further comprises providing a testing piece with the chromotropic acid into the chamber.

3. The detection method as claimed in claim 1, further comprising performing a decompression for the chamber, wherein the chelate is free from a reverse reaction after the decompression.

4. The detection method as claimed in claim 1, further comprising analyzing the chelate, wherein the analyzing the chelate is performed by an analyzing method selected from a group consisting of a titrimetric analysis, a pH value analysis, a conductivity analysis, a spectrum analysis and a combination thereof.

5. The detection method as claimed in claim 1, further comprising a step of analyzing the chelate to determine an original concentration of the airborne molecular substance.

6. The detection method as claimed in claim 1, wherein the performing the cyclic comprises inputting more sample into the chamber.

7. The detection method as claimed in claim 1 further comprising a step of analyzing the chelate, wherein the chromotropic acid is one of a solution and a testing piece and the raising the concentration of the airborne molecular substance and the concentration of the chromotropic acid is performed by a pump.

8. The detection method as claimed in claim 7, wherein the testing piece is a solid chelating agent.

9. The detection method as claimed in claim 1, wherein the providing the chromotropic acid further comprises providing a solution having the chromotropic acid into the chamber.

10. The detection method as claimed in claim 9, wherein the providing the chromotropic acid further comprises adding a buffer solution into the solution having the chromotropic.

11. A detection method for a sample with airborne molecular substance under a clean room setting, comprising steps of:
providing a chromotropic acid into a chamber in reaction with the sample containing the airborne molecular substance from the clean room to form a chelate;
accelerating a reaction of the sample and the chromotropic acid through cyclic pressurization by raising a concentration of the airborne molecular substance to more than 240 times in each cycle of the cyclic pressurization; and
determining the concentration of the airborne molecular substance by taking image pixels of the chromotropic acid and the chelate to generate a pixel data and analyzing the pixel data,
wherein the airborne molecular substance comprises boron or phosphorous, and
wherein the raising the concentration of the airborne molecular substance to more than 240 times in each cycle renders obtaining a detection result from providing the chromotropic acid into the chamber to analyzing the pixel data in less than 10 minutes.

12. The detection method as claimed in claim 11, wherein the cyclic pressurization raises a concentration of the airborne molecular substance to more than 240 times in each cyclic.

13. An instant detection method for airborne molecular substance in a clean room, comprising:
providing a chamber;
providing a chromotropic acid in the chamber, the chromotropic acid being configured to react with the airborne molecular substance from the clean room to form a chelate; and
performing cyclic pressurization through a pumping device coupled to the chamber,
raising a concentration of the airborne molecular to increase a reacting rate of the airborne molecular substance and the chromotropic acid and accumulate the chelate through performing cyclic pressurization by a pump; and
determining the concentration of the airborne molecular substance by taking image pixels of the chromotropic acid and the chelate to generate a pixel data and analyzing the pixel data, wherein the raising the concentration of the airborne molecular substance by performing the cyclic pressurization renders obtaining a detection result from providing the chromotropic acid in the chamber to analyzing the pixel data in less than 10 minutes.

14. The detection method as claimed in claim 13 further comprising providing an automatic motor to drive the pumping device.

15. The detection method as claimed in claim 13 further comprising providing a computer to analyze the chelate.

16. The detection method as claimed in claim 13 further comprising providing a camera to take image pixels for the reagent and the chelate to generate a pixel data.

* * * * *